United States Patent [19]

Ikeda et al.

[11] 4,222,908
[45] Sep. 16, 1980

[54] THIXOTROPIC NAIL ENAMEL

[75] Inventors: Toshihide Ikeda; Toshiaki Kobayashi, both of Yokohama; Motokiyo Nakano, Sagamihara; Chiaki Tanaka, Kawasaki, all of Japan

[73] Assignee: Shiseido Co., Ltd., Tokyo, Japan

[21] Appl. No.: 970,242

[22] Filed: Dec. 18, 1978

[30] Foreign Application Priority Data

Jun. 8, 1978 [JP] Japan ................................ 53/69087

[51] Int. Cl.$^2$ ........................ A61K 7/043; C08L 1/18
[52] U.S. Cl. ................................. 260/16; 260/17 R; 106/181; 106/195; 424/61
[58] Field of Search ................. 424/61; 106/195, 181; 260/16, 17

[56] References Cited

U.S. PATENT DOCUMENTS

| 1,878,477 | 9/1932 | Ellis et al. | 424/61 |
| 3,257,279 | 6/1966 | Schain | 106/195 |
| 3,407,160 | 10/1968 | Frank | 106/271 |
| 3,422,165 | 1/1969 | Kuritzkes | 424/61 |
| 3,864,294 | 2/1975 | Busch, Jr. | 424/61 |

OTHER PUBLICATIONS

Chem. Abst. 71:116,558h.

Primary Examiner—Theodore Morris
Attorney, Agent, or Firm—Miller & Prestia

[57] ABSTRACT

Thixotropic nail enamel comprising, a gelling agent, a gel composition containing a chip composition which is prepared by mixing, under heating and compression, organically modified montmorillonite clay, nitrocellulose, and a substance which is capable of swelling the montmorillonite clay and is capable of plasticizing the nitrocellulose is provided. The thixotropic nail enamel has the advantages that the viscosity thereof does not increase with the lapse of time and the gelling state thereof is stable. This gel composition can also delete toluene and xylene, which must be contained in the conventional nail enamel, from the thixotropic nail enamel of the present invention.

3 Claims, No Drawings

THIXOTROPIC NAIL ENAMEL

The present invention relates to a thixotropic nail enamel.

Nail enamels (or nail lacquers) are film-forming compositions which generally are air-dried at an ambient temperature. Nail enamels containing organically modified montmorillonite clays, which are known as a non-aqueous gelling agent, are well-known in the art.

However, conventional nail enamels generally have the disadvantage that the viscosity thereof gradually increases with the lapse of time. For this reason, the commercial products many times cannot be completely used up, that is, until the contents of the package containing the product is empty.

In order to prevent the separation (or settling) of pigments and pearl essences from nail enamels containing the same, the use of organically modified montmorillonite clays is proposed. For example, U.S. Pat. No. 3,422,185 discloses the use of the organically modified montmorillonite clays for preventing precipitation of pigments and pearl essences in nail enamels, color separation and separation of the constituents of the nail enamels. Japanese Patent Publication (KOKOKU) No. 47-40375/72 discloses that an organically modified montmorillonite clay as well as an inorganic or organic acid are mixed with and dispersed in a cosmetic base for dispersing pearl essences therein. Further, Japanese Laid-Open Application (KOKAI) No. 49-97830/74 discloses gel coating compositions containing an amine type modified montmorillonite clay, a swelling agent, such as orthophosphoric acid, and substances such as acetone, isopropyl alcohol and butyl acetate, which have a polar group and an affinity for other constituents. However, in these conventional nail enamels, since the organically modified montmorillonite clay is simply mixed into the nail enamel base, the nail enamel so obtained has a poor pigment dispersion stability and a poor gloss. This is because the swelling and the dispersion force of the organically modified montmorillonite clay in the nail enamel are poor.

The organically modified montmorillonite clays can be prepared by chemically and interlaminatingly bonding cationic active agents and polar higher organic compounds to the clay mineral (i.e. the montmorillonite clay). The interlaminar distance of the organically modified montmorillonite clay molecule is expanded by the action of a solvent, such as toluene and the like, and swells in the solvent. When the organically modified montmorillonite clays are in the form of powders, agglomerates of the montmorillonite powders are formed. In order to exhibit their inherent effectiveness in the nail enamel, the organically modified montmorillonite clays must be finely and uniformly dispersed in the nail enamel. However, since a simple mechanical dispersion of the organically modified montmorillonite clays into the nail enamel by using, for example, a disper, is not sufficient for complete dispersion of the clay, the gloss and the transparency of the resulting nail enamel film decrease due to the presence of the powder agglomerates of the organically modified montmorillonite clay in the film.

Accordingly, the objects of the present invention are to obviate the afore-mentioned problems of the conventional nail enamels and to provide a novel nail enamel composition, the viscosity of which becomes stable about one week after the preparation and, thereafter, does not increase with the lapse of time.

Another object of the present invention is to provide a novel nail enamel composition which can be completely used up, that is, until the contents of the package containing the product is empty.

In accordance with the present invention, there is provided a nail enamel having dispersed therein, as a gelling agent, a gel composition containing (i) 10 through 30% by weight of a chip composition which is prepared by mixing, under heating and compression, a mixture of (A) 25 through 70% by weight of organically modified montmorillonite clay, (B) 5 through 70% by weight of nitrocellulose and (C) 5 through 30% by weight of a substance which is capable of swelling the component (A) and also capable of plasticizing the component (B), and; (ii) 70 through 90% by weight of an organic mixed solvent.

As mentioned hereinbefore, when the organically modified montmorillonite clays are mechanically dispersed into the nail enamel by using, for example, a disper, the properties, especially the gelling property, of the modified montmorillonite clay can not be improved. However, it has been found that, when organically modified montmorillonite clay is compounded into a chip composition by milling the clay powder with the other ingredients on, for example, a roll mill, under heating and compression, the organically modified montmorillonite agglomerated powders can be deagglomerated and, therefore, can be finely and uniformly dispersed into a nail enamel. As a result, the present nail enamel prepared from this gel composition, containing the organically modified montmorillonite clay thus subjected to the milling treatment, provides a pretty glossy film when it is applied. Thus, loss of the luster of the film and decrease in the transparency of the film due to the presence of the agglomerated powder of the organically modified montmorillonite clay is not observed at all. In view of the previous understanding in the art that clay minerals can afford a good gelling property to nail enamels but function as a certain kind of matte agent, the above-mentioned phenomenon constitutes signficant progress in the art. That is to say, it has been found that the good gelling property of the organically modified montmorillonite clays cannot be exhibited in the nail enamel unless the clays are sufficiently swollen by the penetration of solvents contained in the nail enamel into the interlaminar portions of the microstructure of the clays. Even when the organically modified montmorillonite clays are compounded into a chip composition for nail enamels without mixing (or milling), under heating and compression, the interlaminar distance of the micro structure of the organically modified montmorillonite clays cannot be expanded. Therefore, when such chip composition is added to a nail enamel, the thixotropic property of the clay is not improved in the nail enamel. As a result, although the luster of the film on the fingernail is good, a stable nail enamel cannot be obtained, due to the fact that pigment particles contained in the nail enamel tend to separate and to settle on the bottom of the nail enamel container.

In Japanese Patent Laid-Open Application (KOKAI) No. 52-145528/77 we proposed a process for preparing a gell composition comprising the steps of mixing, under heating and compression, organically modified montmorillonite clays, nitrocellulose, conventional plasticizer (e.g. dibutyl phthalate, acetyl tributyl citrate), and organic solvents which are capable of satisfactorily swelling the organically modified montmorillonite clays, to thereby prepare a chip composition, and; then, incorporating the chip composition into an organic mixed solvent. When the gel composition thus prepared is incorporated into the nail enamel, the nail enamel having a good pigment dispersion stability and a good gelling property, and also, providing a good glossy film, can be obtained. However, since a large amount of organic solvents are vaporized or splashed into the surrounding environment during the milling operation, our above-mentioned prior process is not preferable from economic, environmental health and safety points of view.

Contrary to the above, according to the present invention, since non-volatile substances having a high boiling point are used as substances which are capable of swelling the organically modified montmorillonite clay, the afore-mentioned problems are completely solved. Examples of such substances are:

(i) compounds having a general formula, $HO(RO)_mH$ (wherein R is $C_2H_4$ and $C_3H_6$, and m is an integer of 3 through 90) such as, for example, polyethylene glycol, preferably, having a weight-average molecular weight of about 200 through about 4000, and preferably 300 through 3500, polypropylene glycol, preferably, having a weight-average molecular weight of about 300 through about 5000, and the like, (ii) compounds having a general formula, $R'O(RO)_nH$ (wherein R is $C_2H_4$ and $C_3H_6$, R' is an alkyl group having 4 through 20 carbon atoms and n is an integer of 1 through 50) such as, for example, polyoxyethylene lauryl ether having an ethylene oxide addition molar number of about 8 through about 15, and preferably 8 through 14, polyoxyethylene stearyl ether having an ethylene oxide addition molar number of about 9 through about 15 and the like;

(iii) esters of dicarboxylic acids having 4 through 10 carbon atoms with aliphatic lower alcohols having 1 through 4 carbon atoms, such as, for example, diethyl adipate, dibutyl sebacate and the like. These compounds can be used alone or in any mixture thereof. These compounds can not only swell the organically modified montmorilonite clays in the chip composition, but also plasticize the nitrocellulose. Accordingly, an excellent chip composition suitable for use in the preparation of the nail enamels of the present invention can be obtained only by milling a mixture of (A) 25 through 70% by weight of an organically modified montmorillonite clay, (B) 5 through 70% by weight of nitrocellulose and (C) 5 through 30% by weight of a substance which is capable of swelling the component (A) and is also capable of plasticizing the component (B) under heating and compression conditions.

If the amount of the component (A) is less than 25% by weight, a chip composition having a sufficient gelling property cannot be obtained, whereas if the amount of the component (A) is more than 70% by weight, a composition in the form of a chip cannot be obtained. On the other hand, if the amount of the component (B) is less than 5% by weight, a composition in the form of a chip cannot be obtained, whereas if the amount of the component (B) is more than 70% by weight, a chip composition having a sufficient gelling property cannot be obtained. Further, if the amount of the component (C) is less than 5% by weight, or more than 30% by weight, a composition in the form of a chip cannot be obtained.

The organically modified montmorillonite clays compounded into the chip composition of the present invention can include any known organically modified montmorillonite clays, such as, for example, dimethylbenzyldodecyl ammonium montmorillonite (which is commercially available from National Lead Industries, Inc. as "BENTONE 27"), dimethyldioctadecyl ammonium montmorillonite (which is commercially available from National Lead Industries, Inc. as "BENTONE 38") and the like.

The nitrocellulose compounded into the chip composition of the present invention can include any nitrocellulose which is generally used as a film-forming constituent in conventional nail enamels. Typically, so-called nitrocellulose "¼ second", nitrocellulose "½ second" and the like are used.

In the chip composition disclosed in the above-mentioned Japanese Patent Laid-Open Application (KOKAI) No. 52-145528, substantial amounts of the solvents to be used are vaporized or splashed during the milling operation on milling rolls. Contrary to this, the component (C) of the chip composition of the present invention is present in the chip composition after the milling operation in such a state that the component (C) penetrates into the interlaminar portions of the organically modified montmorillonite clay molecules and swells the clay molecules. Thus, in the subsequent step (i.e. the step in which the chip composition so obtained is dissolved and dispersed in a mixed organic solvent), the mixed solvent can be easily put into the interlaminar portion of the swelled montmorillonite clay, and a good gel composition for nail enamel having a sufficient amount of the mixed solvent in the interlaminar portions of the organically modified montmorillonite clay molecules can be obtained. For this reason, since the organically modified montmorillonite clay is still present in the clear swelling condition in the gel composition of the present invention, a good gelling property is exhibited in the gel composition, and also there is neither separation nor settling of the pigments and the pearl essences in the nail enamel. In addition, since the organically modified montmorillonite clay is finely divided by the milling operation, the film or coating of the fingernail is very lustrous.

The swelling force and the plasticizing force of typical compounds which can swell the organically modified montmorillonite clay and also can plasticize nitrocellulose are shown in Table 3 below.

(a) Determination of Swelling Force

In order to determine the swelling force of the substances listed in Table 3, the substances are separately mixed with "BENTONE 27" (i.e. dimethylbenzyldodecyl ammonium montmorillonite clay) and nitrocellulose "¼ second", in accordance with the compounding ratio (I) shown in Table 1, and then, the mixtures are subjected to a milling treatment on milling rolls to prepare chip compositions. The interlaminar distance (00 1 face) of the organically modified montmorillonite clay contained in the chip composition is measured by means of an X-ray diffraction device (RIGAKU Rota Slex Type RU-3). It was determined by the two inventors of the present invention that the interlaminar distance of BENTONE 27 powder is 9.4 Å and that D.B.P. (i.e. dibutyl phthalate) cannot expand the interlaminar distance of the organically modified montmorillonite clay. In the case of a substance which has sufficient swelling force but has little plasticizing force, the compounding ratio (II) is used. The results are shown in Table 3 below.

TABLE 1

| (% by weight) | | | |
|---|---|---|---|
| I | | II | |
| BENTONE 27 | 47 | BENTONE 27 | 47 |
| Nitrocellulose "¼ second" | 41 | Nitrocellulose "¼ second" | 31 |
| Substance listed in TABLE 3 | 12 | D.B.P. | 10 |
| | | Substance listed in TABLE 3 | 12 |

(b) Determination of Plasticizing Force

In order to determine the plasticizing force of the substances listed in Table 3, chip compositions are prepared in the same manner as described in the above paragraph (a). Each chip composition is then coated onto a glass plate at a film thickness of 0.175 mm by an applicator. After 1 hour, the hardness of the coating is measured by using a Vickers hardness testor (Micro Hardness Testor Type MVK, AKASHI SEISAKU-SHO, JAPAN), under the test conditions of a load of 100 gr, a thickness of the coating of 0.175 mm and a load hold time of 5 seconds, in accordance with the procedure of JIS (Japanese Industrial Standard)-B-7774. The results are shown in Table 3 below. The value of the hardness increases as the hardness of the coating decreases.

TABLE 2

| | (% by weight) |
|---|---|
| Nitrocellulose "¼ second" | 15 |
| Modified alkyd resin | 15 |
| Organic mixed solvent* | 65 |
| Substance listed in TABLE 3 | 5 |

*a mixture of 48% of butyl acetate, 38% of toluene, 10% of ethyl acetate and 4% of n-butyl alcohol.

TABLE 3

| No. | Substance (Sample) | Formulation | Interlaminer Distance (Å) | Hardness of Coating |
|---|---|---|---|---|
| 1 | Polyethylene Glycol (M.W. 200) | I | 22 | 189 |
| 2 | Polyethylene Glycol (M.W. 300) | " | 25 | 185 |
| 3 | Polyethylene Glycol (M.W. 400) | " | 25 | 183 |
| 4 | Polyethylene Glycol (M.W. 600) | " | 21 | 172 |
| 5 | Polyethylene Glycol (M.W. 1000) | " | 21 | 171 |
| 6 | Polyethylene Glycol (M.W. 1500) | " | 18 | 167 |
| 7 | Polyethylene Glycol (M.W. 4000) | " | 15 | 153 |
| 8 | Polyoxyethylene Lauryl Ether (E.O. Add. Mol. No. 8) | " | 18 | 128 |
| 9 | Polyoxyethylene Lauryl Ether (E.O. Add. Mol. No. 9) | " | 17 | 135 |
| 10 | Polyoxyethylene Lauryl Ether (E.O. Add. Mol. No. 15) | " | 14 | 147 |
| 11 | Polyoxyethylene Stearyl Ether (E.O. Add. Mol. No. 9) | " | 20 | 216 |
| 12 | Polyoxyethylene Stearyl Ether (E.O. Add. Mol. No. 15) | " | 16 | 143 |
| 13 | Diethyl Adipate | " | 22 | 155 |
| 14 | Dibutyl Sebacate | " | 19 | 174 |
| 15 | Ethylene Glycol Monobutyl Ether | II | 26 | 85 |
| 16 | Benzyl Alcohol | " | 28 | 81 |
| 17 | Liquid Paraffin | " | 12 | 83 |
| 18 | Polyoxyethylene Oleyl Ether (E.O. Add. Mol. No. 2) | " | 14 | 94 |
| 19 | Butyl Carbitol Acetate | I | 13 | 164 |
| 20 | Diisopropyl Adipate | " | 13 | 129 |
| 21 | Diisobutyl Adipate | " | 13 | 129 |
| 22 | D.B.P. | " | 10 | 118 |
| 23 | Acetyltributyl Citrate | " | 10 | 118 |

Nos. 15–23: Comparative Examples

The substances which can be used as the component (C) in the present invention must have an interlaminar distance of not less than about 16 Å and a Vickers hardness of not less than 110. However, substances such as ethylene glycol monobutyl ether and benzyl alcohol, which have an interlaminar distance of not less than 16 Å, cannot be used as the component (C) in the present chip composition because of their high hardness (i.e. Vickers hardness of less than 110), provided that known plasticizers (e.g. D.B.P.) are compounded into the composition in combination with such substances. On the other hand, substances such as butyl carbitol acetate and diisobutyl adipate, which have an interlaminar distance of less than 16 Å, cannot be used as the component (C) in the present chip composition.

The milling operation of the components (A), (B) and (C) can be carried out by any known techniques. Such techniques are generally used in, for example, the paint and varnish industry, the rubber industry and the like, by using a milling roll, a Bunbury mixer, a colloid mill and the like under compression, at a temperature of about 40° through 70° C.

The gel composition for the nail enamels of the present invention can be prepared by simply and mechanically mixing 10 through 30% by weight of the above-mentioned chip composition with 70 through 90% by weight of an organic mixed solvent. If the amount of the chip composition is less than 10% by weight, or more than 30% by weight, a gel composition which can provide a nail enamel having a suitable viscosity cannot be obtained. On the other hand, if the amount of the organic mixed solvent is less than 70% by weight, or more than 90% by weight, a gel composition which can provide a nail enamel having a suitable viscosity cannot be obtained.

The organic mixed solvents compounded into the gel composition for the nail enamel of the present invention generally include those which can be incorporated into the conventional nail enamel compositions. Examples of such mixed solvents are any mixtures of (a) 30–70% by weight of at least one selected from toluene, xylene, n-hexane, n-heptane and isoparafin having a boiling point of about 70° through about 200° C., and preferably about 100° C. through about 180° C.; (b) 30–70% by weight of at least one selected from butyl acetate, ethyl acetate, methyl ethyl ketone, methyl isobutyl ketone, tetrahydrofuran, ethylene glycol monoethyl ether and (c) 5–20% by weight of at least one selected from ethyl alcohol, acetone, isopropyl alcohol.

The viscosity of conventional nail enamels containing organically modified montmorillonite clay generally tends to gradually increase with the lapse of time. This phenomenon causes the problem that the commercial nail enamels many times cannot be completely used up, as mentioned above. In order to prevent such gradual increase of the viscosity, high amount of a polar solvent, or solvents such as butyl acetate, ethyl acetate, methyl ethyl ketone and methyl isobutyl ketone can be incorporated into the nail enamel. However, even when a higher amount of a polar solvent is used, the viscosity of the nail enamel cannot be kept stable for a long period of time, and in addition, syneresis of the gel, which impairs the effect of the nail enamel product, occurs with the lapse of time. The viscosity change and the gel stability of nail enamels having various compositions shown in Table 4 were tested. The results are shown in Table 5 below.

TABLE 4

| Formulation No. | (% by weight) | | | | |
| --- | --- | --- | --- | --- | --- |
| | 1 | 2 | 3 | 4 | 5 |
| Nitrocellulose | 12 | 12 | 12 | 12 | 12 |
| Modified alkyd resin | 12 | 12 | 12 | 12 | 12 |
| Acetyltributyl citrate | 5 | 5 | 5 | 5 | 5 |
| Organically modified montmorillonile clay* | 1 | 1 | 1 | 1 | 1 |
| Iron oxide pigment | 0.5 | 0.5 | 0.5 | 0.5 | 0.5 |
| Titanium dioxide | 0.1 | 0.1 | 0.1 | 0.1 | 0.1 |
| Toluene | 25 | 15 | 5 | 21 | 17 |
| Butyl acetate | 34.4 | 44.4 | 34.4 | 38.4 | 42.4 |
| Ethyl acetate | 10 | 10 | 10 | 10 | 10 |
| Ethyl alcohol | — | — | — | 4 | 8 |
| Total | (100) | (100) | (100) | (100) | (100) |

*BENTONE 27

TABLE 5

Viscosity Change and Gel Stability v.s. Solvent Composition in Nail Enamel

| Time Period | Formulation No. 1 | | Formulation No. 2 | | Formulation No. 3 | | Formulation No. 4 | | Formulation No. 5 | |
| --- | --- | --- | --- | --- | --- | --- | --- | --- | --- | --- |
| | *1 Viscosity | *2 Stability | *1 Viscosity | *2 Stability | *1 Viscosity | *2 Stability | *1 Viscosity | *2 Stability | *1 Viscosity | *2 Stability |
| 0 | 700 | 0 | 1220 | 0 | 1780 | 0 | 1200 | 0 | 1730 | 0 |
| 1 Day | 1070 | 0 | 1540 | 0 | 2070 | 0 | 1480 | 0 | 1970 | 0 |
| 1 Week | 1050 | 0 | 1840 | 0 | 2180 | −1 | 1800 | 0 | 2090 | −1 |
| 2 Weeks | 1980 | 0 | 2010 | −1 | 2200 | −2 | 2070 | −1 | 2110 | −2 |
| 1 Month | 2510 | 0 | 2130 | −2 | 1990 | −3 | 2200 | −2 | 2030 | −3 |

*1 Centipoise
*2 Gel stability evaluated according to the following scoring criteria.
0: No separation observed.
−1: Little separation observed.
−2: Separation clearly observed.
−3: Remarkable separation observed.

In the organically modified montmorillonite clay, organic cations are ionically attached to the surfaces of the clay minerals, which are charged negative. The most excellent conventional gel contains ⅛ to 1/7 as much polar additives (e.g. ethyl alcohol, acetone) as amount of the organically modified montmorillonite clay and several tens times the amount of the organically modified montmorillonite clay of non-polar solvents (e.g. toluene, xylene). The polar additives are attracted to hydrophilic groups present in the surfaces of the montmorillonite clay, whereby the organic cations of hydrocarbon chains orginally present on the surfaces of the organically modified montmorillonite clay are forced out therefrom. Thus, the interlaminar distances of the montmorillonite clay are somewhat enlarged and a gellation reaction is initiated. On the other hand, the hydrocarbon chains forced out from the surfaces of the montmorillonite clay possess a good affinity for the solvents such as toluene, xylene and the like. Therefore, when a large amount of such solvents is compounded into the gel, the hydrocarbon chains are progressively forced out from the surfaces of the montmorillonite clay and the interlaminar distances of the montmorillonite clay are increasingly expanded. Thus, gellation is accelerated. Toluene, xylene and the like contained in mixed solvents which are usually used in conventional nail enamels accelerate the gellation, whereas alcohols, ketones and the like contained in the mixed solvents which are usually used in conventional nail enamels initiate the gellation reaction. In the case where the compounding ratio of the latter in the mixed solvent increases, the rate of gel formation becomes faster and the subsequent gellation is mildly accelarated. Thus, nail enamels in which the viscosity does not remarkably increase with the lapse of time can be prepared. However, in these nail enamels, since only the hydrocarbon chains are present in the interlaminar portions of the montmorillonite clay, the polar solvents tend to be separated from the gel system and syneresis of the gel occurs with the lapse of time.

Contrary to the aobve, according to the present invention, since the above-mentioned component (C), having a polar property, is present in a stable state, together with hydrocarbon chains, in the interlaminar portions of the organically modified montmorillonite clay, which fact has been confirmed by means of a X-ray diffraction, the polar solvents, even when a large amount of polar solvents are used, can enter into the interlaminar portions of the montmorillonite clay due to the attraction of the polar component (C). Thus, the above-mentioned component (C) of the chip composition of the present invention acts not only as a plasticizing agent for the nitrocellulose, but also as a gelling initiator for the organically modified montmorillonite clay. Accordingly, in the case where the gel composition of the present invention, prepared as mentioned above, is incorporated into nail enamels, nail enamels which exhibit a good gelling property and no increase in viscosity with the lapse of time, and also, which do not cause any separation and settling, can be obtained even when a large amount of polar solvents are incorporated into the nail enamels.

The thixotropic nail enamel of the present invention preferably contains (i) 5 through 20% by weight, and more preferably 10 through 15% by weight, of the gel composition as mentioned above, (ii) 40 through 70% by weight, and more preferably, 50 through 60% by weight of butyl acetate or a mixture of butyl acetate with at least one solvent selected from the group consisting of ethyl acetate, ethyl alcohol, iso-propyl alcohol and butyl alcohol (i.e. solvent system), and (iii) 10 through 55% by weight, and more preferably, 25 through 40% by weight, of the other constituents of the nail enamel. Such constituents generally include a film-forming constituent such as nitrocellulose; resin such as alkyd resin and acrylic resin; plasticizer such as D.B.P. and acetyl tributyl citrate; pigments such as titanium oxide, iron oxides and the like; pearl essences; dyes; UV absorbers; and the like.

In the case where the amount of the gel composition is less than 5% by weight, the afore-mentioned objects of the present invention cannot be fully achieved, whereas in the case where the amount of the gel composition is more than 20% by weight, application properties of the so prepared nail enamels onto a fingernail are unpreferably poor. On the other hand, in the case where the amount of the solvent system is less than 40% by weight, application properties of the so prepared nail enamels onto a fingernail are unpreferably poor, whereas in the case where the amount of the solvent system is more than 70% by weight, covering power of the so prepared nail enamels is insufficient.

In addition, aromatic hydrocarbons, such as toluene, xylene, which must be incorporated into the conventional nail enamels, can be deleted from the nail enamel composition of the present invention, if necessary. This provides a special advantage to the nail enamel because such aromatic hydrocarbon solvents result in the problems that, when nail enamels containing, toluene and/or xylene are frequently coated on very weak fingernails, the fingernails become brittle with the lapse of time and also the fingernails are attacked by an onychoschisis.

The present invention will be further illustrated by, but is by no means limited to, the Examples set forth below. Percentages appearing in the examples are by weight unless otherwise noted.

EXAMPLE 1

A chip composition was prepared by mixing the following ingredients and, then, milling the mixture on two-stage rollers, under heating and compression. The surface temperatures of the rollers were 40° C. (first roll) and 60° C. (second roll).

| Chip Composition | % |
|---|---|
| BENTONE 27 (Dimethylbenzyldodecyl Ammonium Montmorillonite) | 47 |
| Nitrocellulose "¼ second" | 41 |
| Polyethylene Glycol (M.W. 300) | 12 |
| Total | (100) |

18% of the thus prepared composition was then mixed with 82% of a mixed solvent having the following composition.

| Mixed Solvent Composition | % |
|---|---|
| Isopropyl Alcohol | 19 |
| Toluene | 39 |
| n-Butyl Acetate | 42 |
| Total | (100) |

The chip composition was dissolved and dispersed in the mixed solvent to prepare a gel composition.

EXAMPLE 2

A gel composition was prepared from 18% of a chip composition having the following composition and 82% of mixed solvent having the following composition by following the same procedure as mentioned in Example 1.

| Chip Composition | % |
|---|---|
| BENTONE 27 | 48 |
| Nitrocellulose "½ second" | 42 |
| Polyethylene Glycol (E.O. Addition Molar Number:9) | 10 |
| Total | (100) |
| Mixed Solvent Composition | % |
| Isopropyl Alcohol | 18 |
| Toluene | 38 |
| n-Butyl Acetate | 44 |
| Total | (100) |

EXAMPLE 3

A gel composition was prepared from 18% of a chip composition having the following composition and 82% of a mixed solvent having the following composition by following the same procedure as mentioned in Example 1.

| Chip Composition | % |
|---|---|
| BENTONE 38 (Dimethyloctadecyl Ammonium Montmorillonite) | 47 |
| Nitrocellulose "½ second" | 40 |
| Diethyl Adipate | 13 |
| Total | (100) |
| Mixed Solvent Composition | % |
| Isopropyl Alcohol | 17 |
| n-Hexane | 31 |
| n-Butyl Acetate | 52 |
| Total | (100) |

EXAMPLE 4

A gel composition was prepared from 18% of a chip composition having the following composition and 82% of a mixed solvent having the following composition by following the same procedure as mentioned in Example 1.

| Chip Composition | % |
|---|---|
| BENTONE 27 | 47 |
| Nitrocellulose "¼ second" | 41 |
| Polyethylene Glycol (M.W. 300) | 12 |
| Total | (100) |
| Mixed Solvent Composition | % |
| n-Butyl Acetate | 43 |
| Isopropyl Alcohol | 18 |
| ISOPAR E* | 21 |
| Tetrahydrofuran | 18 |
| Total | (100) |

*Branched Hydrocarbon (Isoparaffin) is commercially available ESSO Chemicals.

COMPARATIVE EXAMPLE 1

In a mixed solvent of 15.6% of isopropyl alcohol, 32.0% of toluene and 34.4% of n-butyl acetate, 7.3% of nitrocellulose "¼ second" was dissolved, and then 2.2% of polyethylene glycol (M.W. 300) and 8.5% of BENTONE 27 (i.e. dimethylbenzyldodecyl ammonium montmorillonite) were added to the solution. Thus, a uniform gel composition was prepared after mixing.

COMPARATIVE EXAMPLE 2

Following the same procedure as mentioned in Example 1, a gel composition was prepared from 18% of a chip composition having the following composition and 82% of a mixed solvent having the following composition.

| Chip Composition | % |
| --- | --- |
| BENTONE 27 | 44 |
| Nitrocellulose "¼ second" | 40 |
| D.B.P. (Dibutyl Phthalate) | 16 |
| Total | (100) |
| Mixed Solvent Composition | % |
| Isopropyl Alcohol | 19 |
| Toluene | 39 |
| n-Butyl Acetate | 42 |
| Total | (100) |

Thus, the gel composition in which polyethylene glycol in the gel composition of Example 1 was replaced with a conventional plasticizer, D. B. P. was prepared.

The gel composition prepared in Examples 1 through 4 and Comparative Examples 1 and 2 were evaluated with respect to glossiness and transmission. The results are shown in Table 6 below.

TABLE 6

| | Glossiness (%)[*1] | Transmission (%)[2] |
| --- | --- | --- |
| Example 1 | 73.8 | 87.0 |
| Example 2 | 72.2 | 85.4 |
| Example 3 | 68.5 | 75.8 |
| Example 4 | 70.3 | 77.7 |
| Comparative Example 1 | 2.4 | 30.9 |
| Comparative Example 2 | 73.9 | 86.6 |

[*1] After each gel composition was applied by an applicator onto a clear polyvinyl chloride sheet to prepare a uniform film thereon, surface glossiness of the uniform film was determined by using specular surface technique (angle of incidence 60°, angle of reflection 60°). The value of the glossiness is based on that of the clear polyvinyl chloride sheet, which is considered to have a glossiness of 100%.

[*2] After each gel composition was applied by an applicator onto a clear polyvinyl chloride film to prepare a uniform film having a thickness of 0.425 mm, the transmission of each sample was determined by using a Hitachi Spectrophotometer Type 124 (Hitachi SEISAKUSHO, TOKYO). The wavelength of the light which was used for the determination was 520 mu. The value of the transmission is based on that of the clear polyvinyl chloride sheet, which is considered to have a transmission of 100%.

As will be clear from Table 6, both the glossinesses and transmissions of the gel compositions prepared in Examples 1 through 4 according to the present invention are superior to those of Comparative Example 1. Since the sample of Comparative Example 2 was subjected to the roll treatment, the glossiness and transmission thereof were also good.

EXAMPLES 5 THROUGH 8 AND COMPARATIVE EXAMPLES 3 AND 4

Using the gel compositions prepared in Examples 1 through 4 and also in Comparative Examples 1 and 2, nail enamel compositions were prepared in a conventional manner in accordance with the compounding ratio shown in Table 7 below. The nail enamel compositions were evaluated with respect to the viscosity change and gel stability (separation and settling) with the lapse of time, as well as the gloss of the coating or film when they were applied onto a fingernail. The results are shown in Table 8 below.

TABLE 7

| | (% by weight) | | | | | |
| --- | --- | --- | --- | --- | --- | --- |
| | Example | | | | Comparative Example | |
| Composition | 5 | 6 | 7 | 8 | 3 | 4 |
| Nitrocellulose | 12 | 12 | 12 | 12 | 12 | 12 |
| Modified alkyd resin | 12 | 12 | 12 | — | 12 | 12 |
| Acrylic resin | — | — | — | 12 | — | — |
| Acetyltributyl citrate | 5 | 5 | 5 | 5 | 5 | 5 |
| Methyl ethyl ketone | — | 12 | — | — | — | — |
| n-Butyl acetate | 32.4 | 20.4 | 32.4 | 32.4 | 32.4 | 32.4 |
| Ethyl acetate | 16 | 16 | 16 | 16 | 16 | 16 |
| Ethyl alcohol | 4 | 4 | 4 | 4 | 4 | 4 |
| n-Butyl alcohol | 2 | 2 | 2 | 2 | 2 | 2 |
| Toluene | — | — | — | — | — | — |
| Iron oxide pigment | 0.5 | 0.5 | 0.5 | 0.5 | 0.5 | 0.5 |
| Titanium dioxide | 0.1 | 0.1 | 0.1 | 0.1 | 0.1 | 0.1 |
| Pearl essence | 4.0 | 4.0 | 4.0 | 4.0 | 4.0 | 4.0 |
| Gel composition | | | | | | |
| Example 1 | 12 | | | | | |
| Example 2 | | 12 | | | | |
| Example 3 | | | 12 | | | |
| Example 4 | | | | 12 | | |
| Comparative Example 1 | | | | | 12 | |
| Comparative Example 2 | | | | | | 12 |
| Total | (100) | (100) | (100) | (100) | (100) | (100) |

TABLE 8

| | Change with lapse of time | | | | | | | Gloss |
| --- | --- | --- | --- | --- | --- | --- | --- | --- |
| Example No. | 0 | 1 Day | 1 Week | 2 Weeks | 1 Month | 2 Months | 3 Months | (%) |
| Example 5 | | | | | | | | |
| Viscosity *1 | 1380 | 1690 | 1800 | 1820 | 1780 | 1820 | 1820 | |
| Separation *2 | 0 | 0 | 0 | 0 | 0 | 0 | 0 | 85.0 |
| Settling *2 | 0 | 0 | 0 | 0 | 0 | 0 | 0 | |
| Example 6 | | | | | | | | |
| Viscosity | 1510 | 1840 | 1990 | 2000 | 1970 | 2020 | 2000 | |
| Separation | 0 | 0 | 0 | 0 | 0 | 0 | 0 | 81.7 |
| Settling | 0 | 0 | 0 | 0 | 0 | 0 | 0 | |
| Example 7 | | | | | | | | |
| Viscosity | 1100 | 1320 | 1410 | 1420 | 1420 | 1410 | 1420 | |
| Separation | 0 | 0 | 0 | 0 | 0 | 0 | 0 | 85.5 |
| Settling | 0 | 0 | 0 | 0 | 0 | 0 | 0 | |
| Example 8 | | | | | | | | |
| Viscosity | 970 | 1140 | 1300 | 1310 | 1280 | 1280 | 1330 | |
| Separation | 0 | 0 | 0 | 0 | 0 | 0 | 0 | 87.0 |
| Settling | 0 | 0 | 0 | 0 | 0 | 0 | 0 | |
| Comparative Example 3 | | | | | | | | |
| Viscosity | 200 | 200 | 200 | 200 | 200 | 200 | 200 | |
| Separation | 0 | −1 | −2 | −2 | −3 | −3 | −3 | 18.1 |
| Settling | 0 | −2 | −3 | −3 | −3 | −3 | −3 | |
| Comparative Example 4 | | | | | | | | |
| Viscosity | 200 | 270 | 740 | 940 | 870 | 740 | 705 | |
| Separation | 0 | 0 | 0 | 0 | −2 | −2 | −3 | 86.5 |
| Settling | 0 | 0 | −1 | −1 | −2 | −2 | −3 | |

*1: centipoise
*2: 0 ... Good, −1 ... Fair, −2 ... Poor, −3 ... very poor

Since the gel compositions prepared in Examples 1 through 4 contain, as a gelling initiator, the polar substance (i.e. the component (C)), in the nail enamels of Examples 5 through 8 which contain those gel compositions, an increase in viscosity of the nail enamels with the lapse of time was not observed and the gel stability was excellent. Contrary to this, the nail enamels of Comparative Examples 3 and 4, which contain the gel compositions of Comparative Examples 1 and 2, respectively, did not exhibit a thixotropic property and, therefore, the settling of the pigments and the pearl essence contained therein unpreferably occurs. This is because the gel composition of Comparative Example 1 was not subject to the milling treatment although it contained the organically modified montmorillonite clay together with nitrocellulose and the polar component (C), and because the gel composition of Comparative Example 2 contains the conventional plasticizer (D. B. P.), in lieu of the component (C), which can swell the organically modified montmorillonite clay.

As is clear from the nail enamel of Examples 7 and 8, which contains no conventional aromatic hydrocarbon solvent (e.g. toluene, xylene), even when no aromatic hydrocarbon solvent is contained in the nail enamel, a good gel stability is obtained, and also, an increase in the viscosity of the nail enamel with the lapse of time is not observed at all.

With respect to the gloss of the coatings or films, good results were obtained, except for the nail enamel of Comparative Example 3, containing the gel composition of Comparative Example 1 which was not subjected to the milling treatment.

It is known that, when the compounding ratio of the polar solvent in the nail enamel increases, the thixotropic property of the nail enamel is advantageously improved. Thus, the nail enamel of the present invention has the further advantages that coating property thereof is good and the nail enamel can be easily and smoothly coated onto the surface of a fingernail by a coating brush.

In order to evaluate the thixotropic property of the nail enamel according to the present invention, the ratio of the viscosity of the nail enamel at 6 rpm to that at 60 rpm was measured. The results are shown in the following Table 9.

TABLE 9

|  | Example No. | | | Reference *2 |
| --- | --- | --- | --- | --- |
|  | 5 | 6 | 7 | Example |
| *1 Viscosity at 6 rpm/ Viscosity at 60 rpm | 4.3 | 4.2 | 4.2 | 2.9 |

NOTE:
*1 The viscosity was measured by using B-Type Viscometer (Tokoyo KEIKI SEIZOSHO, TOKYO), at a temperature of 30° C. As is clear from Table 9, the nail enamels of the present show a good thixotropic property.
*2 The sample of the Reference Example was prepared in the manner as described in Example 5, except that a mixture of 25.4% of n-butyl alcohol, 6% of ethyl acetate, 2% of n-butyl alcohol and 21.0% of toluene is used as a solvent constituent.

As a result of a safety test with respect to the nail enamels according to the present invention, it was confirmed that the nail enamels of the present invention can be safely applied to the fingernail.

In the case where the nail enamels of Example 5 (containing no extra toluene) and Example 7 (containing no toluene) as well as Reference Example (containing a large amount of toluene) were daily applied to the skins of guinea pigs for ten days, there was no change in the guinea pigs skins in the case of nail enamel of Examples 5 and 7, whereas severe Desquamation and fissure were observed from 5 days after the application in the case of nail enamel of Reference Example.

What we claim is:

1. A thixotropic nail enamel comprising dispersed therein,
    (1) as a gelling agent, a gel composition containing:
        (i) 10 through 30% by weight of a chip composition which is prepared by mixing, under heating and compression, a mixture of
            (A) 25 through 70% by weight of organically modified montmorillonite clay,
            (B) 5 through 70% by weight of nitrocellulose, and
            (C) 5 through 30% by weight of at least one substance selected from the group consisting of compounds having a general formula:
                $HO(RO)_mH$, wherein R is $C_2H_4$ and $C_3H_6$ and m is an integer of 3 through 90;
                $R'O(RO)_nH$, wherein R is $C_2H_4$ and $C_3H_6$, R' is an alkyl group having 4 through 20 carbon atoms and n is an integer of 1 through 50; and
                esters of dicarboxylic acids having 4 through 10 carbon atoms with aliphatic lower alcohols having 1 through 4 carbon atoms; and
        (ii) 70 through 90% by weight of an organic mixed solvent,
    (2) at least one non-aromatic solvent and;
    (3) as a film forming agent a synthetic gel resin and nitrocellulose.

2. A thixotropic nail enamel as claimed in claim 1, wherein said enamel contains (i) 5 through 20% by weight, based on the total weight of the nail enamel, of said gel composition, (ii) 40 through 70% by weight, based on the total weight of the nail enamel, of butyl acetate or a mixture of butyl acetate with at least one solvent selected from the group consisting of ethyl acetate, ethyl alcohol, iso-propyl alcohol and butyl alcohol, and (iii) 10 through 55% by weight, based on the total weight of the nail enamel.

3. A thixotropic nail enamel as claimed in claim 2, wherein said gel composition does not contain any aromatic hydrocarbon solvent including toluene and xylene.

* * * * *